(12) United States Patent
Zougari (10) Patent No.: US 7,523,648 B2
(45) Date of Patent: Apr. 28, 2009

(54) APPARATUS AND METHODS FOR SOLIDS DEPOSITION AND ANALYSIS

(75) Inventor: Mohammed I. Zougari, Edmonton (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 176 days.

(21) Appl. No.: 11/674,700

(22) Filed: Feb. 14, 2007

(65) Prior Publication Data

US 2008/0190180 A1    Aug. 14, 2008

(51) Int. Cl.
*G01N 33/18* (2006.01)
(52) U.S. Cl. ..................................... 73/61.62
(58) Field of Classification Search ............... 73/61.62, 73/53.01, 841, 54.28
See application file for complete search history.

(56) References Cited

U.S. PATENT DOCUMENTS

| | | | |
|---|---|---|---|
| 3,080,747 A | | 3/1963 | Herman |
| 4,383,438 A | * | 5/1983 | Eaton ........................ 73/61.62 |
| 6,062,069 A | * | 5/2000 | Panchal et al. ............. 73/53.01 |
| 6,535,796 B1 | * | 3/2003 | Sierro et al. ................ 700/281 |
| 6,938,464 B1 | * | 9/2005 | Bi .............................. 73/54.28 |
| 6,959,588 B2 | | 11/2005 | Zougari |
| 7,150,183 B2 | | 12/2006 | Kharrat |
| 7,380,442 B2 | * | 6/2008 | Colaco Covas et al. .... 73/54.28 |
| 7,392,842 B2 | * | 7/2008 | Morgan et al. ........... 166/250.1 |
| 2003/0136184 A1 | * | 7/2003 | Walters et al. ............. 73/54.28 |

* cited by examiner

*Primary Examiner*—Daniel S Larkin
(74) *Attorney, Agent, or Firm*—Jeffrey L. Wendt; Wayne I. Kanak (57) ABSTRACT

Apparatus and methods are described for solids deposition study. One apparatus embodiment of the invention comprises an internal and an external cylinder positioned between first and second end portions, at least one of the cylinders being rotatable and thus forming a Couette-Taylor cell, the internal cylinder having an exterior surface, the external cylinder having an internal surface, an annular sample flow-through chamber or cell formed between the surfaces, optionally the chamber having an adaptable flow-through chamber geometry, the device having a sample inlet and outlet; and a non-intrusive probe for detecting solids deposition on at least one of the surfaces during sample flow through the apparatus. Apparatus described may be used to studying solids deposition from heavy hydrocarbon oils, hydrates, and other high viscosity compositions. This abstract complies with rules requiring an abstract. It should not be used to limit the scope or meaning of the claims.

28 Claims, 6 Drawing Sheets

APPARATUS AND METHODS FOR SOLIDS DEPOSITION AND ANALYSIS

BACKGROUND OF THE INVENTION

1. Field of Invention

The present invention relates generally to the field of solids deposition on surfaces, and more particularly to apparatus and methods for producing layers of solids deposits under continuous flow conditions as a function of influencing variables including, but not limited to flow rate, temperature, pressure, shear, surface type, surface roughness, chemical inhibitors and chemical inducers. The apparatus and methods are useful for predicting solids deposition from fluids including, but not limited to reservoir hydrocarbon and aqueous based fluids, drilling muds, frac fluids, emulsions, and the like, which may have multiple phases (solid, liquid, gas, and combinations thereof).

2. Related Art

Oil fields flow assurance characterizes the operability and reliability of oil and/or gas production systems. Organic and inorganic solids (wax, asphaltenes, hydrates, scale, and the like) precipitation, deposition, emulsion, foaming, corrosion, erosion, inhibition, rheology, and complex multi-phase flow are some of the key issues related to flow assurance. Many flow problems are due to hydrates, wax, asphaltene and scale precipitation, which may lead to deposition on internal pipe and other equipment surfaces, causing pressure reduction, slower production, and ultimately plugging. Moreover, elevated viscosity at low temperatures (gelling) represents potential rheological problems, which may lead to slugging.

One aspect of "flow assurance" is managing the precipitation and deposition formation of these solids: wax, asphaltene, scales, hydrates, among many others. Even though solids precipitation is a prelude to solids deposition, their presence can be passive if proper measures are taken to avoid their adhesiveness to surfaces. It is now proven that any solids deposition occurrence can be a function of any of the following parameters: composition, viscosity, production rate, system pressure, system temperatures, and presence of water, deposition surface type and deposition surface roughness. Solutions to remediate the deposition problem vary from mechanical design to chemical injection. The economic implication, if wrong assessments are made, can be very serious and lead to significant losses due to slow production or shut down. Even though the subject of oil production has been well investigated, the tools to predict and conceptually design the production system, including pipelines, based on reliable experimental measurements and evaluation are very few. So far, very limited and unreliable experimental predictive methods and approaches are available to assess and quantify the wax deposition process, especially under various actual pipeline conditions and/or reservoir conditions. Most available methods fall short in mimicking the actual pipeline turbulent conditions in general, especially at relatively high Reynolds number and high shear. For the asphaltene deposition process, only one known tool, known under the trade designation OSDC (discussed below) is available to trigger and measure deposition under real pipelines conditions of shear, pressure and temperature. There are no known tools or devices available to evaluate, predict, measure or produce scale and hydrates deposits under transport conditions whether at steady state or transient.

Schlumberger has used the system known as the Organic Solids Deposition and Control system (OSDC), described more fully in U.S. Pat. Nos. 6,959,588 and 7,150,183, to identify, produce and control both wax and asphaltene deposits at very realistic reservoir as well as transport conditions. The experimental results using the system known as OSDC were benchmarked against field data and were found to be conservative, yet superior when compared to any other methods such as flow loops, cold finger and stirring tanks. Feedback from major oil companies was very encouraging. The experimental data from live oils, which are expensive to sample, are invaluable.

Despite success of the apparatus known under the trade designation OSDC, the system has numerous limitations in terms of being capable to meet the fast-growing and continuously evolving market. The high cost of the live oil sample collection and its uniqueness make it challenging and crucial for the industry to minimize the risks of not only losing the sample, but most importantly to extract the maximum information possible from it. Better controllability, more powerful hardware, improved design and enhanced geometry are desired to achieve ideal data quality and greater profitability.

SUMMARY OF THE INVENTION

In accordance with the present invention, apparatus and methods for producing layers of solids deposits on a surface under continuous flow conditions as a function of influencing variables are presented. Influencing variables include, but are not limited to flow rate, temperature, pressure, shear, surface type, surface roughness, chemical inhibitors and chemical inducers. The apparatus and methods are useful for predicting solids deposition from fluids including, but not limited to reservoir hydrocarbon and aqueous based fluids, drilling muds, frac fluids, emulsions, and the like, which may have multiple phases (solid, liquid, gas, and combinations thereof). The sample may comprise compositions comprising hydrocarbons (including sour hydrocarbons which may include hydrogen sulfide, mercaptans, and other sulfur-containing compounds), water, organic and/or inorganic solids, and may include micelles, macromolecules, globules, resins, asphaltenes, hydrocarbon and aqueous based fluids, drilling muds, frac fluids, and the like having multiple phases (solid, liquid, gas, and any combination thereof). The sample composition may comprise one or more of each phase. Stated differently, a sample composition may comprise one or more liquid phases, one or more solid phases, and/or one or more gaseous phases.

A first aspect of the invention are apparatus, one apparatus comprising:

(a) an internal and an external cylinder positioned between first and second end portions, at least one of which is rotatable and thus forming a Couette-Taylor device, the internal cylinder having an exterior surface, the external cylinder having an internal surface, an annular sample flow-through chamber or cell formed between the surfaces, optionally the chamber having a variable volume, the device having a sample inlet and outlet; and (b) a non-intrusive probe for detecting solids deposition on at least one of the surfaces during sample flow through the apparatus.

As used in herein, the phrase "non-intrusive probe" means a technique that does not physically touch or otherwise come in physical contact with the sample or the solids deposit. Exemplary non-intrusive probes include acoustic probes, thermal probes, and the like. One suitable thermal probe is a Peltier device. Apparatus within the invention are capable of evaluating samples at temperatures ranging from −40° C. or less up to 250° C. or greater, and pressure ranging from partial vacuum tip to 100 MPa, while at unlimited high shear conditions. Certain apparatus within the invention may have adaptable flow through chamber geometry, meaning that the sample flow through chamber may be modified in volume and/or shape, either off-line, or, more importantly online during solids deposition. The volume of the flow-through chamber may be changed, for example, by changing radius of the inner cylinder (sometimes referred to herein as a spindle), changing radius of the outer cylinder, or both, or by screwing top and/or bottom portions of the cell into or out of the cell body. In certain embodiments, only a potion of the flow-through chamber may be variable in volume and/or shape. In other apparatus within the invention, the internal and external cylinders, as well as any other component exposed to a sample, may be $H_2S$ compatible. Apparatus within the invention include those comprising a flow meter and flow controller affording the operator the option of producing a variable or continuous flow condition, while varying one or more other independent influencing variables, including but not limited to, temperature, pressure, shear, surface type, surface roughness, chemical composition, such as inclusion of inhibitors and chemical inducers (for example water, solvents, and the like). Apparatus of the invention may include one or more chemical injection nozzles, attached to pumps and reservoirs of various fluids that may be added to the virgin sample flowing through the chamber. Apparatus of the invention may include nozzles for injection of gases, liquids, slurries, emulsions, and solids in the form of solutions. Certain apparatus within the invention are capable of performing solids deposition monitoring and analysis at any flow regime including multiphase flow (gas-liquid-solid). Certain apparatus of the invention may include an external cylinder having an internal surface, exposed to the flowing sample. which has two or more surface types and surface roughness. Other apparatus of the invention may include a removable solids deposition surface. Apparatus within the invention may be outfitted with connections allowing the apparatus to be fastened to a completion tool or other downhole tool, or pipe or tubing, such as coiled tubing. Certain embodiments of apparatus of the invention may be suitable for use on a working hydrocarbon oil or gas rig. Apparatus within the invention may include a variable torque motor for varying the torque of the rotating cylinder (interior or exterior, or both through suitable gearing), allowing apparatus of the invention to investigate solids deposits from heavy hydrocarbon oils, hydrates, and other high viscosity compositions.

Apparatus within the invention may comprise thermal energy supply able to transfer heat faster to the flow-through chamber than previously known apparatus, while improving insulation to avoid heat losses. Apparatus within the invention may exhibit reduced depletion effect due to mass balance, while the flow-through design allows the apparatus to mimic actual production piping. Certain apparatus within the invention may include one or more sub-components for detection and quantification of precipitates in the sample chamber. Suitable sub-components for detection an quantification of precipitates include, but are not limited to detectors based on optical methods, acoustic methods, ultrasonic methods, visual methods, and the like. Apparatus of the invention may analyze single and multi-phase flowing samples. Apparatus within the invention may analyze flowing samples depositing one or more solids (mono- and co-deposition), wherein the co-deposition may be layered (one deposit overlapping another deposit) or non-layered (one deposit in one surface location and another deposit in a different surface location). Apparatus within the invention may also simulate commingled fluids through the provision of suitable nozzles, pumps, and other and flow connections.

Apparatus within the invention include those wherein fluid connections between the inlet and the sample chamber, and the outlet and the sample chamber are selected from mechanical barriers, interfacial barriers and any other form of barrier that would prevent the sample and deposits collected being contaminated by the non-sampled material. An example of a mechanical barrier may be an elastomeric membrane; an example of an interfacial barrier may be an interface between two immiscible fluids.

As noted previously, apparatus within the invention include those wherein the sample chamber is able to change volume and/or shape. This may be accomplished through a joint that allows a moveable portion of the outer cylinder to be moved in 3-dimensional space, including in translational movements (x, y, z) or by cylindrical movements (circular, radial and translational) or equivalent. The movement of the moveable portion of the outer cylinder may be performed manually or automatically, for example, through computer control. The moveable portion of the outer cylinder may be fluidly connected to a system allowing two-way flow of a fluid to effect movement of the moveable outer cylinder portion.

Another aspect of the invention are methods of precipitating and depositing one or more solid samples from a primary sample, one method comprising:
  (a) flowing a sample into a flow-through Couette-Taylor apparatus of the invention, the interior and exterior cylinders of the apparatus comprising materials capable of maintaining temperatures and pressures in the flow-through chamber at least different than ambient conditions, and in certain embodiments representative of a hydrocarbon-bearing reservoir a hydrocarbon-bearing reservoir;
  (b) forming at least one precipitate in the flow-through sample chamber; and
  (c) depositing at least one of the precipitates on at least one of the surfaces.

Methods within this aspect of the invention include those wherein the forming and/or depositing steps comprise manipulating one or more include those comprising a flow meter and flow controller affording the operator the option of producing a variable or continuous flow condition, while varying one or more other independent influencing variables, including but not limited to, temperature, pressure, shear, surface type, surface roughness, chemical composition, such as inclusion of inhibitors and chemical inducers allowing the sample probe to be moved in 3-dimensional space, including in translational movements (x, y, z) or by cylindrical movements (circular, radial and translational) or equivalent, inside of the primary chamber.

Yet another aspect of the invention are methods of manipulating one or more particles in a primary sample at non-ambient conditions, one method comprising:
  (a) flowing a sample into a flow-through Couette-Taylor apparatus of the invention, the interior and exterior cylinders of the apparatus comprising materials capable of maintaining temperatures and pressures in the flow-through chamber at least different than ambient conditions, and in certain embodiments representative of a hydrocarbon-bearing reservoir a hydrocarbon-bearing reservoir; and
  (b) detecting solids deposition on at least one of the surfaces during sample flow through the apparatus using a non-intrusive probe.

Methods within this aspect of the invention include those wherein the non-intrusive probe is selected from acoustic probes, thermal probes, and the like, although the invention is not so limited.

Apparatus and methods of the invention will become more apparent upon review of the detailed description of the invention and the claims that follow.

BRIEF DESCRIPTION OF THE DRAWINGS

The manner in which the objectives of the invention and other desirable characteristics may be obtained is explained in the following description and attached drawing in which.

It is to be noted, however, that the appended drawings are not to scale and illustrate only typical embodiments of this invention, and are therefore not to be considered limiting of its scope, for the invention may admit to other equally effective embodiments.

DETAILED DESCRIPTION

In the following description, numerous details are set forth to provide an understanding of the present invention. However, it will be understood by those skilled in the art that the present invention may be practiced without these details and that numerous variations or modifications from the described embodiments may be possible.

As noted previously herein, despite success of Schlumberger's apparatus known under the trade designation OSDC, the system has numerous limitations in terms of being capable to meet the fast-growing and continuously evolving market. Apparatus and methods of the present invention address one or more of the following limitations of the OSDC: non-adaptability (limited scalability to mimic available pipelines, non-transferable to field or downhole, and fixed, single-type deposition surface incapable of multi-surface deposit buildup); single phase process only; static and non-refreshed processed oil sample (no fresh feed or feed-through); bulky geometry; limitation to wax and asphaltene deposition performance, with high conservatism for asphaltene deposition (not appropriate for scales, hydrates, and heavy oil); limited heat balance process system; limited heater heat transfer performance; extreme heat loss; slow heat transfer; limited torque; inability of detecting and monitoring any deposition buildup; high depletion aspect ratio factor; conservative output; weak collection procedure of processed sample for analytical work; inability of processing sample quantification through good mass balance; no co-deposition performance; no commingling performance; crude injection process, requiring chemicals, one or more pressurized gases, or other fluids.

In contrast, apparatus and methods of use of the invention have one or more of the following features/advantages. Apparatus and methods of the invention may employ a non-intrusive probe for detecting the presence of deposits, and measuring the amount and type of deposits. Exemplary non-intrusive probes include acoustic probes, thermal probes, and the like. The deposition surface or surfaces may be removed from apparatus of the invention. Apparatus within the invention are capable of evaluating samples at temperatures ranging from −40° C. or less up to 250° C. or greater, and pressure ranging from partial vacuum up to 100 MPa, while at unlimited high shear conditions. Certain apparatus within the invention may have adaptable flow through chamber geometry, meaning that the sample flow through chamber may be modified in volume and shape, either offline, or, more importantly online during testing. The volume of the flow-through chamber may be changed, for example, by changing radius of the inner cylinder (sometimes referred to herein as a spindle), changing radius of the outer cylinder, or both. In certain embodiments, only a potion of the flow-through chamber may be variable in volume and/or shape. In other apparatus within the invention, the internal and external cylinders, as well as any other component exposed to a sample, may be $H_2S$ compatible. Apparatus within the invention include those comprising a flow meter and flow controller affording the operator the option of producing a variable or continuous flow condition, while varying one or more other independent influencing variables, including but not limited to, temperature, pressure, shear, surface type, surface roughness, chemical composition, such as inclusion of inhibitors and chemical inducers (for example water, solvents, and the like). Apparatus of the invention may include one or more chemical injection nozzles, attached to pumps and reservoirs of various fluids that may be added to the virgin sample flowing through the chamber. Apparatus of the invention may include nozzles for injection of gases, liquids, slurries, emulsions, and solids in the form of solutions. Certain apparatus within the invention are capable of performing solids deposition monitoring and analysis at any flow regime including multiphase flow (gas-liquid-solid). Certain apparatus of the invention may include an external cylinder having an internal surface, exposed to the flowing sample, which has two or more surface types and surface roughness. Other apparatus of the invention may include a removable solids deposition surface. Apparatus within the invention may be outfitted with connections allowing the apparatus to be fastened to a completion tool or other downhole tool, or pipe or tubing, such as coiled tubing. Certain embodiments of apparatus of the invention may be suitable for use on a working hydrocarbon oil or gas rig. Apparatus within the invention may include a variable torque motor for varying the torque of the rotating cylinder (interior or exterior, or both through suitable gearing), allowing apparatus of the invention to investigate solids deposits from heavy hydrocarbon oils, hydrates, and other high viscosity compositions.

Apparatus within the invention may comprise thermal energy supply able to transfer heat faster to the flow-through chamber than previously known apparatus, while improving insulation to avoid heat losses. Apparatus within the invention may exhibit reduced depletion effect due to mass balance, while the flow-through design allows the apparatus to mimic actual production piping. Certain apparatus within the invention may include one or more sub-components for detection and quantification of precipitates in the sample chamber. Suitable sub-components for detection an quantification of precipitates include, but are not limited to detectors based on optical methods, acoustic methods, ultrasonic methods, visual methods, and the like. Apparatus of the invention may analyze single and multi-phase flowing samples. Apparatus within the invention may analyze flowing samples depositing one or more solids (mono- and co-deposition), wherein the co-deposition may be layered (one deposit overlapping another deposit) or non-layered (one deposit in one surface location and another deposit in a different surface location). Apparatus within the invention may also simulate commingled fluids through the provision of suitable nozzles, pumps, and other and flow connections.

Figure 1:
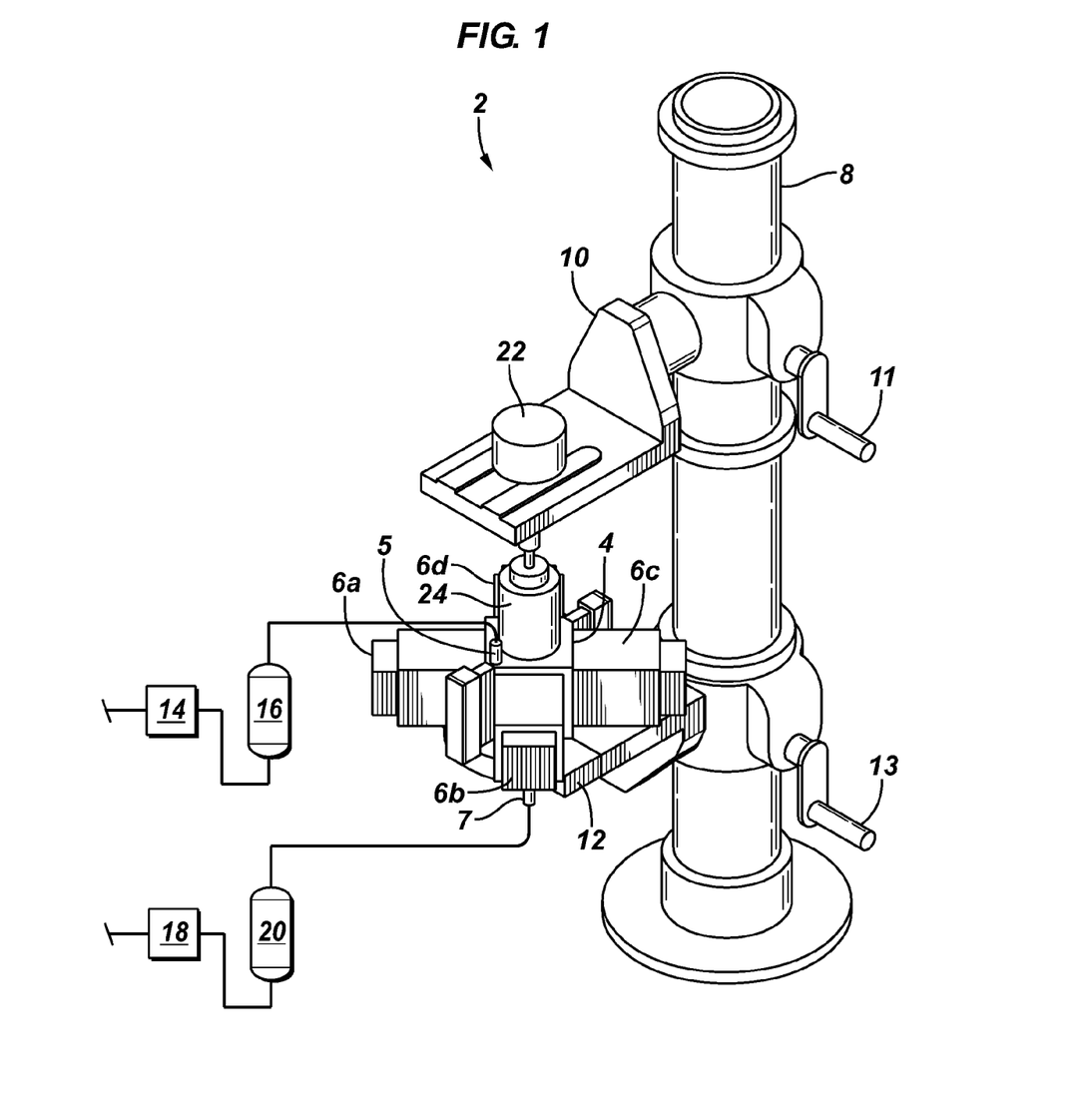
FIG. 1 is a schematic perspective view of an apparatus within the invention.

FIG. 1 illustrates in schematic perspective view one apparatus embodiment 2 within the invention. It will be recognized by those skilled in the art that not all of the features in the embodiments described herein may be necessary in all embodiments. Embodiment 2 comprises a cell body 4 and sample inlet/outlet connections 5 and 7. Either connection may serve as inlet or outlet, depending primarily on the particular sample being tested, the deposits being investigated, and the wishes of the user. Also illustrated in this embodiment are four cooling fans 6a, 6b, 6c, and 6d, used for cooling an exterior cylinder and its interior wall surface (not illustrated in FIG. 1). Cell body 4 and cooling fans 6 are supported in this embodiment by a post or stand 8 including adjustable platforms 10 and 12. Handles 11 and 13 allow adjustment of the platforms 10 and 12, respectively, up and down as desired. Platform 10 supports a motor 22, which may be a variable torque motor, for turning a coupling 24. Coupling 24 is magnetically coupled to a spindle (not illustrated in this embodiment) inside cell body 4. Also illustrated are pumps 14 and 18, as well as fluid accumulators 16 and 20, which may be of any suitable type. Pumps 14, 18 and accumulators 16, 20 allow inflow and outflow of fluid through tubing 9, and allow an operator of the apparatus to maintain a precise volume and pressure in cell body 4.

Figure 2:
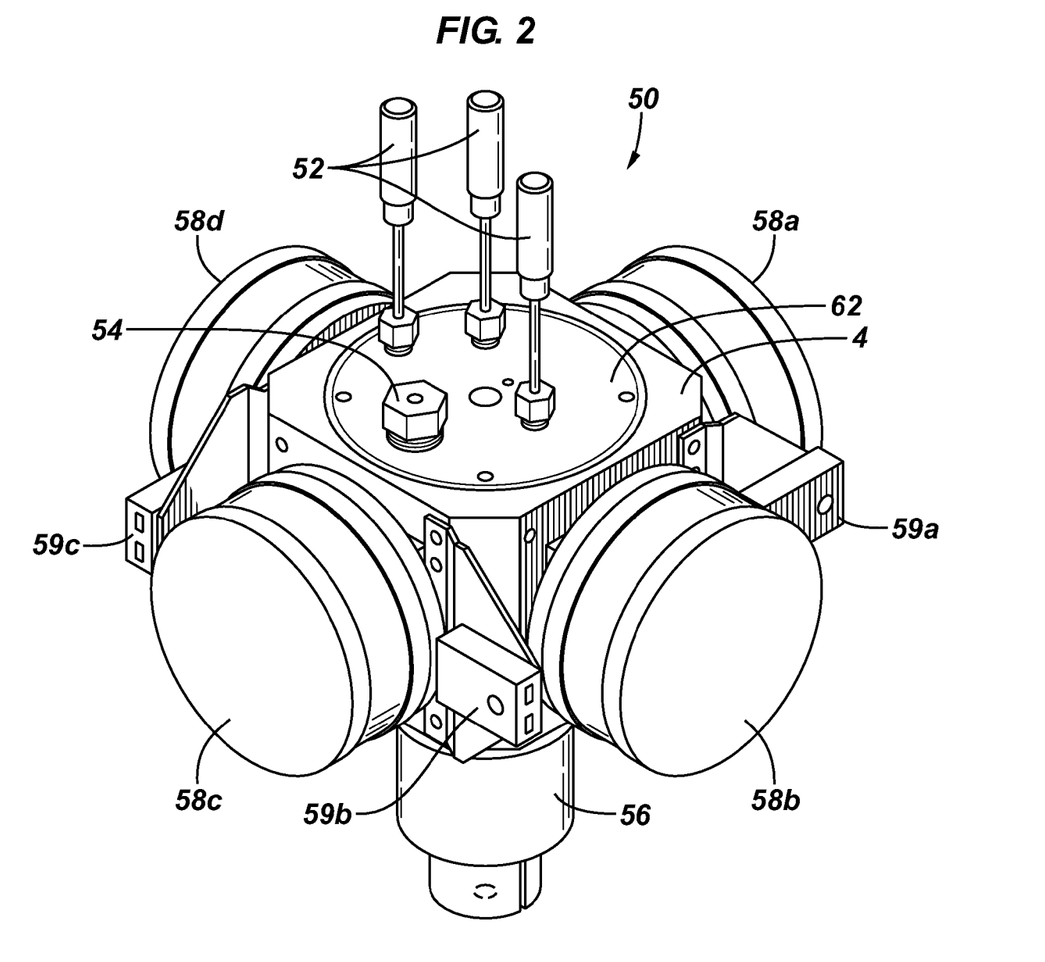
FIG. 2 is a schematic perspective view of a sample cell of another apparatus within the invention.
Figure 3:
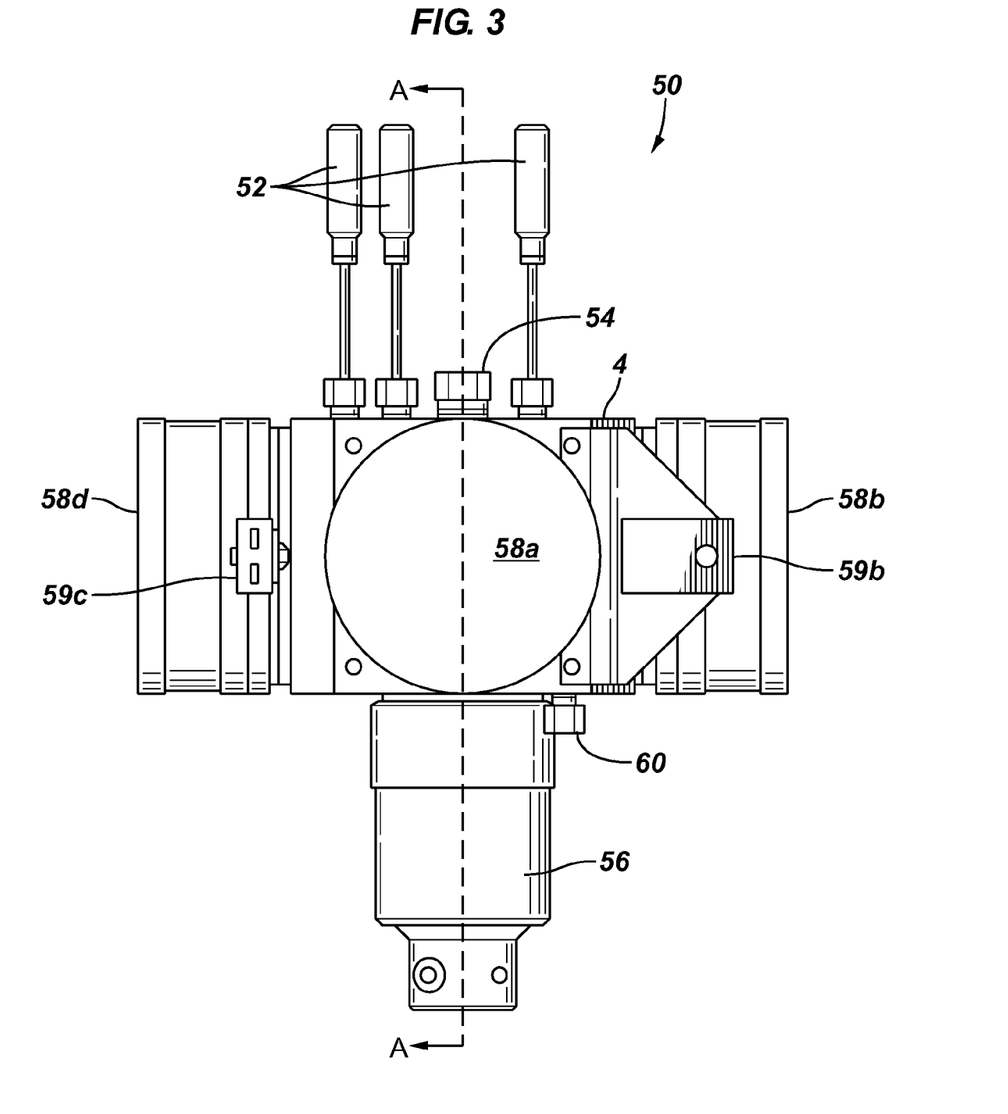
FIG. 3 is a schematic side elevation view of the sample cell of FIG. 2.

FIG. 2 is a schematic perspective view of a sample cell of another apparatus 50 within the invention. Cell body 4 as illustrated in this embodiment is essentially a metal box having top and bottom portions 62, 64, screwed therein (see FIG. 4). Thermocouples 52 allow temperature measurement in side of cell body 4. Inlet/outlet connection 54 is visible in FIG. 2, but inlet/outlet connection 60 is not (see FIG. 3). Coupling 56 is essentially the same as coupling 24 in embodiment 2 (FIG. 1). Embodiment 50 differs from embodiment 2 in having liquid-cooled Peltier cells 58a, 58b, 58c, and 58d, rather than cooling fans. The plumbing for the liquid cooling is not illustrated. Four foil thermocouple plugs 59a, 59b, 59c, and 59d are attached to body 4 by corresponding brackets. Four RTDs may also be potted into cell body. FIG. 3 is a schematic side elevation view of the sample cell of FIG. 2. offering a view of inlet/outlet connections 54 and 60. FIG. 3 also illustrates a line A-A for the cross-sectional view of FIG. 4.

Figure 4:
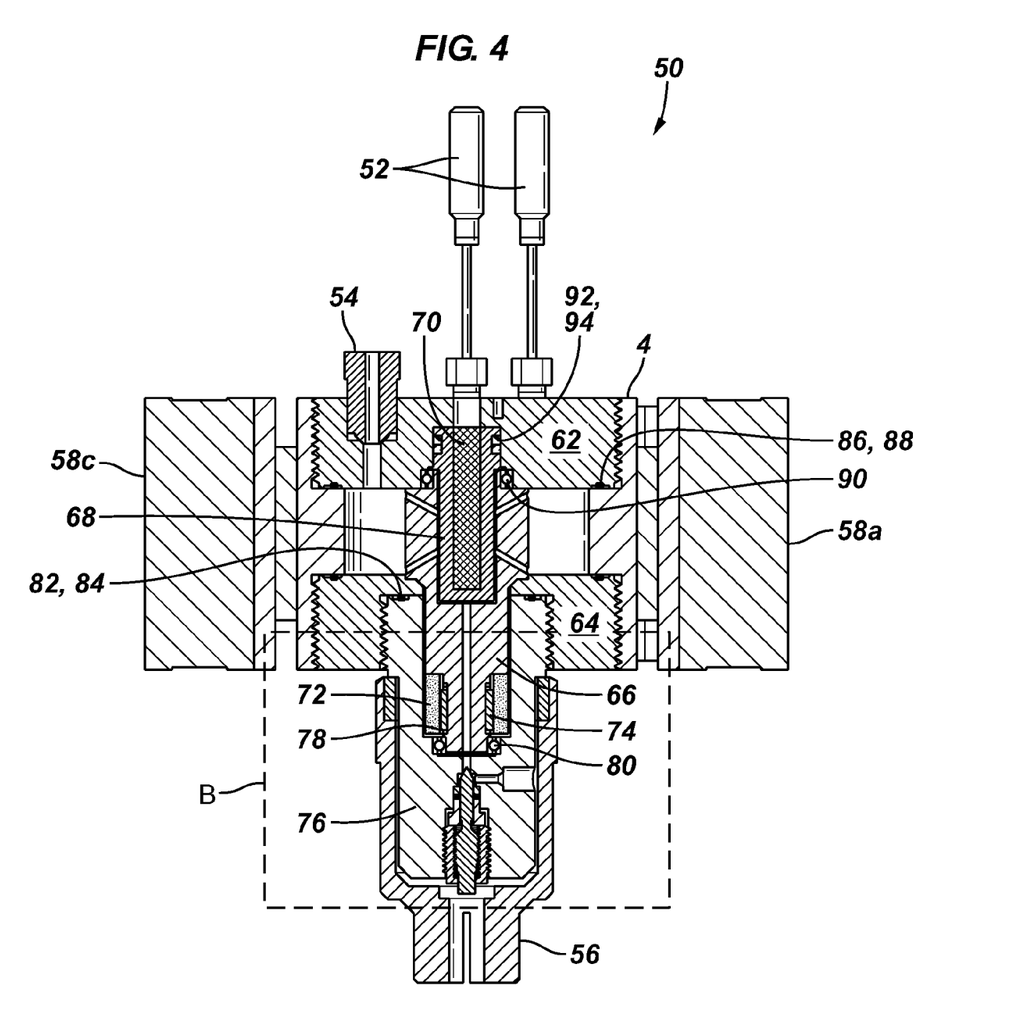
FIG. 4 is a cross-sectional view of the sample cell of FIG. 3 taken along line A-A of FIG. 3.

FIG. 4 is a cross-sectional view of the sample cell of FIG. 3 taken along line A-A of FIG. 3. Illustrated is sample cell 4, top and bottom portions 62, 64, respectively, of sample cell 4, and a spindle or inner cylinder 66. Inside of spindle 66 in this embodiment is an electrical (capacitance) heater 68 and heater core 70. An inner magnet assembly 72 serves to magnetically couple with coupling 56 during use of the apparatus for sample testing. One or more shims 74 may be used to keep inner magnet assembly 72 and spindle aligned vertically and provide stability for spindle 66. A capacitance magnet 76 provides the magnetic force for the magnetic coupling. Two keys 78 are provide for locking in shims Bottom and top bearings 80 and 90, respectively, are provided for spindle 66. Bearings 80, 90 may be steel ceramic, or steel-ceramic hybrid bearings. Also present are double seals 82, 84, and 86, 88. In these double seals, a first, inner polymeric seal 82 and 86 (comprising polymers such as that known under the trade designation Viton, a fluoroelastomer) and backup ring seals 84, 88 are provided. Backup seals 84 and 88 may be metallic, polymeric, or other type of seals. A similar double seal is provided for the heater 68, at 92, 94.

Figure 5:
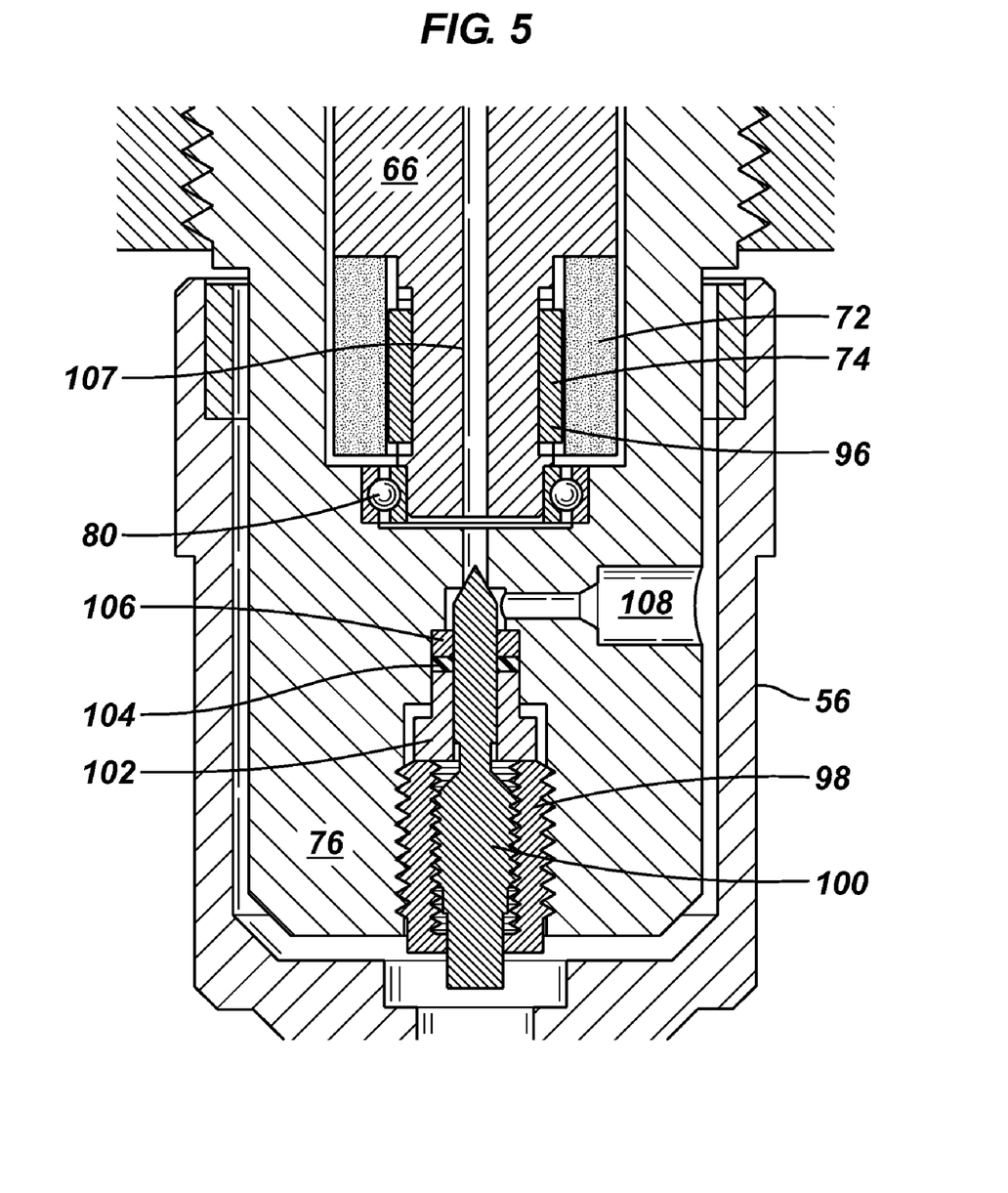
FIG. 5 is a schematic cross-sectional view of area "B" of FIG. 4.

FIG. 5 is a schematic cross-sectional view of area "B" of FIG. 4, illustrating a lower portion 96 of shim 74 rising on lower bearing 80, as well as a nut gland 98, a valve stem 100, a pair of washers 102, 106, and a valve packing 104. The function of valve stem 100 will be explained when describing the operation of this embodiment.

Figure 6:
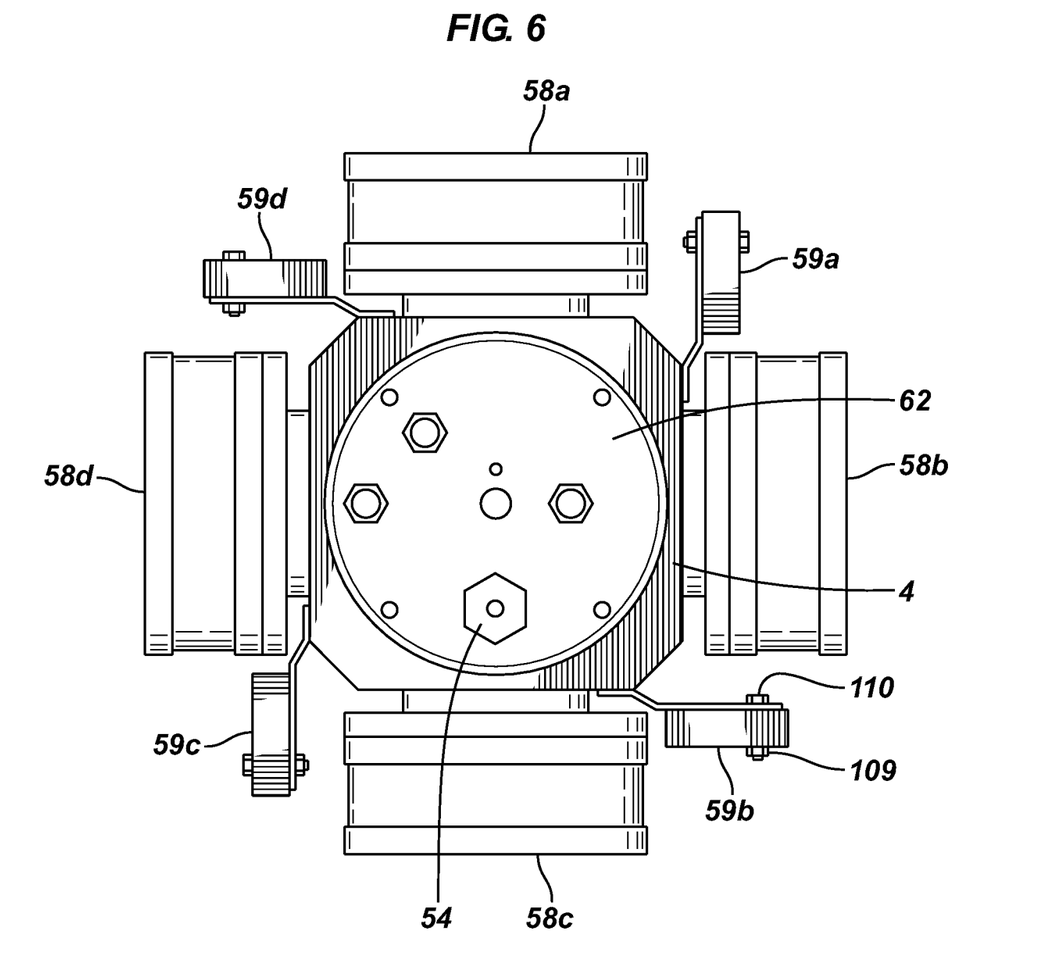
FIG. 6 is a schematic plan view of the sample cell of FIG. 2.

FIG. 6 is a schematic plan view of the sample cell of FIG. 2, illustrating another view of the cell body, as well as bolt 110 and nut 109 attachments for foil thermocouples 59.

Sample cell 4 and top and bottom portions 62, 64 may be manufactured using the same or similar high-temperature, high-pressure corrosion resistant materials. In certain embodiments, the entire apparatus may be temperature controlled. Sources of temperature control include liquid baths, liquid jackets, peltier devices, convection gas baths, and the like. For example, a convection air bath may be employed to control the temperature in the entire apparatus to within ±1° C., and in certain embodiments within ±0.1° C. If vibration is to be minimized, apparatus of the invention may be isolated from its surrounding to minimize vibration of the apparatus.

In operation of apparatus of the invention, the sample chamber defined by inner surfaces of the cell body 4 and top and bottom portions 62, 64, and outside surfaces of spindle 66, is pumped full of a pre-test fluid, or a fluid to be tested. In one arrangement, the fluid flows in through inlet/outlet connection 54, into the sample chamber and out through a tube 107 and a nozzle 108. During this step, cap 56 is not present, and valve stem 100 is backed down to allow fluid to traverse through tube 107 and out through nozzle 108. This is continued until the operator is satisfied with pressure, temperature, and other conditions within the test cell. Then valve stem 100 is moved up to close off tube 107 from nozzle 108, and cap 56 installed and fitted to a motor (not illustrated). Connection 60 is opened, and flow of sample started, as well as the motor to begin rotation of the spindle while sample is flowing through the sample cell. Solids may precipitate and deposit on surfaces with in the cell.

The minimum size or volume of the sample cell may be as low as 15 cc, whereas the sample cell may have a volume of 500 cc or higher, depending on the tests to be run and the amount of sample collected. For these and other reasons, sample testing and solids deposition using apparatus and methods of the invention may be automated.

Sample compositions from which solids may be studied may be gaseous, liquid, supercritical, and any combination thereof. The sample may comprise any sample at elevated temperatures and pressures, including, but not limited to compositions comprising hydrocarbons (including sour hydrocarbons which may include hydrogen sulfide, mercaptans, and other sulfur-containing compounds), water, organic and/or inorganic solids, and may include micelles, macromolecules, globules, resins, waxes, asphaltenes, hydrocarbon and aqueous based fluids, drilling muds, frac fluids, and the like having multiple phases (solids, liquid, and gas). The sample composition may comprise one or more of each phase. The term "reservoir" may include hydrocarbon deposits accessible by one or more wellbores. A "wellbore" includes cased, cased and cemented, or open-hole wellbores, and may be any type of well, including, but not limited to, a producing well, a non-producing well, an experimental well, an exploratory well, and the like. Wellbores may be vertical, horizontal, any angle between vertical and horizontal, diverted or non-diverted, and combinations thereof, for example a vertical well with a non-vertical component. The phrase "high temperature, high pressure" means any temperature and pressure conditions that are above atmospheric pressure and above 20° C.

Asphaltenes are heavy, highly aromatic molecules that often precipitate from oils due to reductions in pressure and/ or temperature or blending with incompatible fluids (see A. Hammami and J. Ratulowski in: Asphaltenes, Heavy Oils and Petroleomics, Oliver C. Mullins, Eric Y. Sheu, Ahmed Hammami, Alan Marshall, Editors, Kluwer Academic Publications, PRECIPITATION AND DEPOSITION OF ASPHALTENES IN PRODUCTION SYSTEMS: A FLOW ASSURANCE OVERVIEW, Chapter 23, 2006). Asphaltenes also contain multiple polar compounds; including oxygen, nitrogen, and sulphur that make the asphaltene molecules surface active. This surface activity leads to asphaltene deposition on the walls of process equipment and transportation pipelines and allows asphaltene to participate in the stabilization of water-in-oil emulsions. The "strength" of the surface activity of individual asphaltene molecules is dependent on the variation in asphaltene composition. There is experimental evidence that a small, specific sub-fractions of the asphaltene is responsible for the deposits found on solid surfaces (see, for example, M. Zougari, S. Jacobs, A. Hammami, G. Broze, M. Flannery, J. Ratulowski and A. Stankiewicz, "Novel Organic Solid Deposition and Control Device for Live Oils: Design and Applications" Energy & Fuels, 20 (2006) 1656-1663).

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. An apparatus comprising:
   (a) an internal and an external cylinder positioned between first and second end portions, at least one of which is rotatable and thus forming a Couette-Taylor cell, the internal cylinder having an exterior surface, the external cylinder having an internal surface, an annular sample flow-through chamber or cell formed between the surfaces, the flow-through chamber having an adaptable flow-through geometry wherein the flow-through chamber may be modified in volume and/or shape, the device having a sample inlet and outlet; and
   (b) a non-intrusive probe for detecting solids deposition on at least one of the surfaces during sample flow through the apparatus.

2. The apparatus of claim 1 wherein the non-intrusive probe is selected from optical probes, acoustic probes, thermal probes, ultrasonic probes, and combinations thereof.

3. The apparatus of claim 2 wherein the non-intrusive probe is a thermal probe, and the thermal probe is a Peltier device.

4. The apparatus of claim 1 wherein the sample flow-through chamber may be modified either off-line or online during solids deposition.

5. The apparatus of claim 4 wherein the volume of the flow-through chamber is changeable by changing the radius of the inner cylinder, changing the radius of the outer cylinder, or both, and by screwing the first and second end portions of the cell further into or out of the cylinders.

6. The apparatus of claim 4 wherein the sample chamber is able to change volume and/or shape manually or automatically through a joint that allows a movement of a portion of the first and/or second end portions.

7. The apparatus of claim 1 wherein at least the internal and external cylinders, and first and second end portions of the cell are $H_2S$ compatible.

8. The apparatus of claim 1 comprising one or more sample flow components connected to the inlet and outlet, the flow components selected from pumps, accumulators, flow meters and flow controllers affording an operator the option of producing a variable or continuous flow condition, while varying one or more other independent influencing variables, including, but not limited to, temperature, pressure, shear, surface type, surface roughness, and sample chemical composition.

9. The apparatus of claim 8 comprising one or more chemical injection nozzles attached to one of the flow components, allowing one or more compositions to be added to a sample flowing through the chamber.

10. The apparatus of claim 1 wherein the external cylinder internal surface comprises two or more surface types and surface roughness.

11. The apparatus of claim 1 comprising a removable solids deposition surface.

12. The apparatus of claim 1 comprising connections allowing the apparatus to be fastened to a completion tool or other oilfield tool, pipe or tubing, such as coiled tubing.

13. The apparatus of claim 1 comprising a variable torque motor for varying torque applied to at least one of the interior and exterior cylinder.

14. The apparatus of claim 1 comprising a thermal energy supply able to transfer heat to the flow-through chamber.

15. The apparatus of claim 1 comprising one or more hear sinks thermally connected to the cell.

16. The apparatus of claim 1 comprising one or more fluid seal connections between the inlet and the sample chamber and the outlet and the sample chamber, the fluid seal connections selected from mechanical barriers, interfacial barriers and any other form of barrier that would prevent the sample and deposits collected being contaminated by the non-sampled material.

17. An apparatus for measuring solids deposition from a sample at non-ambient conditions, comprising:
   (a) a rotatable spindle positioned generally internal of an external cylinder, the spindle and external cylinder removably positioned between top and bottom end portions, thus forming a Couette-Taylor cell, the spindle having an exterior surface, the external cylinder having an internal surface, an annular sample flow-through chamber or cell formed between the surfaces, the chamber having an adaptable flow-through chamber geometry, the device having a sample inlet and outlet; and
   (b) a variable torque motor for rotating the spindle;
   (c) one or more non-intrusive probes for detecting solids deposition on at least one of the surfaces during sample flow through the cell;
   (d) a thermal energy supply removably positioned generally inside of the spindle; and
   (e) one or more heat sinks thermally connected to the cell.

18. The apparatus of claim 17 wherein the non-intrusive probe is selected from optical probes, acoustic probes, thermal probes, ultrasonic probes, and combinations thereof.

19. The apparatus of claim 17 wherein the non-intrusive probe is a thermal probe, and the thermal probe is a Peltier device.

20. The apparatus of claim 17 wherein the external cylinder internal surface comprises two or more surface types and surface roughness.

21. The apparatus of claim 17 comprising connections allowing the apparatus to be fastened to a completion tool or other oilfield tool, pipe or tubing, such as coiled tubing.

22. A method comprising:
   (a) flowing a sample into a flow-through Couette-Taylor cell comprising an internal and an external cylinder positioned between first and second end portions, wherein at least one of said cylinders is rotatable, the internal cylinder having an exterior surface, the external cylinder having an internal surface, an annular sample flow-through chamber or cell formed between the surfaces, the flow-through chamber having an adaptable flow-through geometry wherein the flow-through chamber may be modified in volume and/or shape, the device having a sample inlet and outlet, and a non-intrusive probe for detecting solids deposition on at least one of the surfaces during sample flow through the apparatus;

(b) forming at least one precipitate in the flow-through sample chamber; and (c) depositing at least one of the precipitates on at least one of the surfaces.

23. The method of claim 22 wherein the forming and/or depositing steps comprise manipulating one or more flow meters and/or flow controllers affording an operator the option of producing a variable or continuous flow condition, while varying one or more other independent influencing variables selected from temperature, pressure, shear, surface type, surface roughness, and sample chemical composition.

24. The method of claim 22 comprising mimicking actual production piping flow conditions during the forming and depositing steps.

25. The method of claim 22 comprising detecting and quantifying precipitates in the sample chamber, using methods selected from optical methods, acoustic methods, ultrasonic methods, visual methods, and combinations thereof.

26. The method of claim 22 comprising analyzing multiphase flowing samples.

27. The method of claim 22 comprising depositing more than one solid deposit, wherein the solid deposits may be selected from layered and non-layered deposits.

28. The method of claim 22 wherein the sample comprises heavy hydrocarbon oils, hydrates, and other high viscosity compositions.

* * * * *